United States Patent [19]

Kita et al.

[11] Patent Number: 5,024,930

[45] Date of Patent: Jun. 18, 1991

[54] SILVER HALIDE PHOTOGRAPHIC LIGHT-SENSITIVE MATERIAL CONTAINING A NOVEL PHOTOGRAPHIC COUPLER

[75] Inventors: Hiroshi Kita, Hachioji; Hajime Wada, Tokyo; Yutaka Kaneko, Sagamihara, all of Japan

[73] Assignee: Konica Corporation, Tokyo, Japan

[21] Appl. No.: 523,876

[22] Filed: May 16, 1990

[30] Foreign Application Priority Data

May 18, 1989 [JP] Japan .................................. 1-125052

[51] Int. Cl.$^5$ .............................................. G03C 7/38
[52] U.S. Cl. .................................. 430/558; 430/384; 430/385
[58] Field of Search .................. 430/558, 558 A, 384, 430/385, 548

[56] References Cited

U.S. PATENT DOCUMENTS

| | | | |
|---|---|---|---|
| 2,299,641 | 10/1942 | Middleton et al. | 430/558 |
| 3,841,880 | 10/1974 | Kertel | 430/558 |
| 4,430,423 | 2/1984 | Aoki et al. | 430/558 |
| 4,950,585 | 8/1990 | Tachibana et al. | 430/385 |

FOREIGN PATENT DOCUMENTS 2085851 3/1990 Japan .................................. 430/558

OTHER PUBLICATIONS

Research Disclosure, RD12140, May 1974.

*Primary Examiner*—Charles L. Bowers, Jr.
*Assistant Examiner*—Lee C. Wright
*Attorney, Agent, or Firm*—Finnegan, Henderson, Farabow, Garrett and Dunner

[57] ABSTRACT

There is disclosed a silver halide light-sensitive photographic material containing a novel coupler represented by the following Formula I:

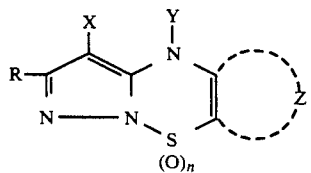

wherein R represents a hydrogen atom or a substituent; X and Y represent independently a hydrogen atom or a group capable of splitting off upon a reaction with an oxidation product of a developing agent; Z represents a benzene ring, a naphthalene ring or a the group of atoms necessary to form a 5 to 7-membered heterocyclic ring; and n represents an integer of 1 or 2.

9 Claims, No Drawings

SILVER HALIDE PHOTOGRAPHIC LIGHT-SENSITIVE MATERIAL CONTAINING A NOVEL PHOTOGRAPHIC COUPLER

FIELD OF THE INVENTION

The present invention relates to a silver halide photographic light-sensitive material containing a novel photographic coupler, more particularly to a silver halide photographic light-sensitive material containing a photographic coupler capable of forming a dye image of excellent fastness to heat, moisture and light.

BACKGROUND OF THE INVENTION

When a silver halide photographic light-sensitive material (hereinafter referred to as a light-sensitive material) is exposed imagewise and then developed, a dye image is formed on an exposed area by the reaction of an oxidation product of an aromatic primary amine color developing agent with a dye-forming coupler.

In this photographic system, a color reproduction technique based on the subtractive process is generally used to form yellow, magenta and cyan dye images.

Examples of photographic couplers useful for forming a yellow dye image are acylacetanilide couplers; those of couplers useful for forming a magenta dye image are pyrazolone, pyrazolobenzimidazole, pyrazorotriazole and indazolone couplers; and those of cyan dye image-forming couples are phenol and naphthol couplers.

The resulting dye image is required to be free from fading and discoloration even if exposed to light or stored under a high temperature and a high humidity for a long time.

The phenol and naphthol couplers for forming a cyan dye image are liable to be unsatisfactory in such characteristics as spectral absorption, heat resistance and moisture resistance. Though various approaches including studies on the substituent have been attempted to solve the above problems, they have not necessarily been successful so far.

SUMMARY OF THE INVENTION

The object of the present invention is to provide a light-sensitive material containing a novel photographic coupler.

Another object of the present invention is to provide a light-sensitive material containing a photographic coupler which is capable of forming a dye image free from discoloration and fading caused by exposure to heat, moisture or light.

The above objects can be attained by a light-sensitive material containing the photographic coupler represented by the following Formula I:

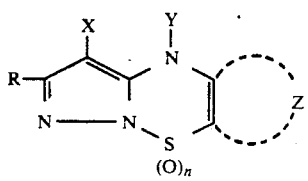

wherein Z represents a non-metallic atomic group necessary to form a 5- to 7-membered heterocycle, a benzene ring or a naphthalene ring; X and Y independently represent a hydrogen atom and a group capable of being split off upon a reaction with an oxidation product of a color developing agent; R represents a hydrogen atom or a substituent; and n represents 1 or 2.

DETAILED DESCRIPTION OF THE INVENTION

The substituent represented by R in Formula I is an alkyl, aryl, anilino, acylamino, sulfonamide, alkylthio, arylthio, alkenyl, and cyclohexyl groups. Other examples are a halogen atom; a cycloalkenyl, alkynyl, heterocyclic, sulfonyl, sulfinyl, phosphonyl, acyl, carbamoyl, sulfamoyl, cyano, alkoxy, aryloxy, heterocyclicoxy, siloxy, acyloxy, sulfonyloxy, carbamoyloxy, amino, alkylamino, imide, ureido, sulfamoylamino, alkoxycarbonylamino, aryloxycarbonylamino, alkoxycarbonyl, aryloxycarbonyl, heterocyclicthio, thioureido, carboxy, hydroxy, mercapto, nitro, and sulfo groups; and a spiro residue and a bridged hydrocarbon residue.

In the above groups represented by R, the alkyl group has preferably 1 to 32 carbon atoms, and may be linear or branched; the aryl group is preferably a phenyl group; the acylamino group includes alkylcarbonylamino and arylcarbonylamino group; the sulfonamide group includes alkylsulfonylamino and arylsulfonylamino groups; the alkyl and aryl components in the alkylthio and arylthio groups are the above alkyl and aryl groups represented by R; the alkenyl group has preferably 2 to 32 carbon atoms; the cycloalkyl group has preferably 3 to 12, more preferably 5 to 7 carbon atoms; the cycloalkenyl group has preferably 3 to 12, more preferably 5 to 7 carbon atoms; the sulfonyl group includes an alkylsulfonyl and arylsulfonyl groups; the sulfinyl group includes alkylsulfinyl and arylfulfinyl groups; the phosphonyl group includes alkylphosphonyl, alkoxyphosphonyl, aryloxyphosphonyl and arylphosphonyl groups; the acyl group includes alkylcarbonyl and arylcarbonyl groups; the carbamoyl group includes alkylcarbamoyl and arylcarbamoyl groups; the sulfamoyl group includes alkylsulfamoyl and arylsulfamoyl groups; the acyloxy group includes alkylcarbonyloxy and arylcarbonyloxy groups; the sulfonyloxy group includes alkylsulfonyloxy and arylsulfonyloxy groups; the carbamoyloxy group includes alkylcarbamoyloxy and arylcarbamoyloxy groups; the ureido group includes alkylureido and arylureido groups; the sulfamoylamino group includes alkylsulfamoylamino and arylsulfamoylamino groups; the heterocyclic group is preferably a 5- to 7-membered ring such as 2-furyl, 2-thienyl, 2-pyrimidinyl, 2-benzothiazolyl, 1-pyrolyl and 1-tetrazolyl; the heterocyclicoxy group is preferably a 5- to 7-membered ring such as 3,4,5,6-tetrahydropyranyl-2-oxy and 1-phenylterazole-5-oxy; the heterocyclicthio group is preferably a 5- to 7-membered ring such as 2-pyridylthio, 2-benzothiazolylthio and 2,4-diphenoxy-1,3,5-triazole-6-thio; the siloxy group includes trimethylsiloxy, triethylsiloxy and dimethylbutylsiloxy; the imide group includes succinimide, 3-heptadecyl succinimide, phthalimide and gultarimide; the spiro residue includes spiro[3,3]heptane-1-yl; the bridged hydrocarbon residue includes bicyclo[2,2,1]heptane-1-yl, tricyclo[3,3,1,13,7]decane-1-yl and 7,7-dimethyl-bicyclo[2,2,1]heptane-1-yl.

Further, the foregoing groups may have a non-diffusible substituent such as a long-chain hydrocarbon group or a polymer residue.

The groups represented by X are a halogen atom, a hydrogen atom, alkyl, alkoxy, aryloxy, heterocyclicoxy, acyloxy, sulfonyloxy, alkoxycarbonyloxy, aryloxycarbonyl, alkyloxalyloxy, alkoxyoxalyloxy, alkylthio, arylthio, heterocyclicthio, alkyloxythiocarbonylthio, acylamino, sulfonamide, nitrogen-containing heterocycle having a bonding site on N, alkyloxycarbonylamino, aryloxycarbonylamino and carboxyl groups, and a group represented by:

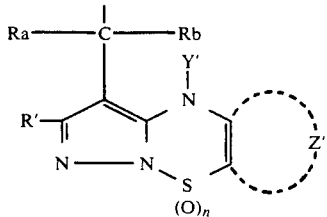

wherein R', Y' and Z' represent the same as those defined for R, Y and Z in Formula I, respectively; n is 1 or 2; and Ra and Rb independently represent a hydrogen atom, an aryl group, an alkyl group and a heterocyclic group.

Among these groups, preferable one is a halogen or hydrogen atom.

Y represents a hydrogen atom or a group capable of being split off upon a reaction with an oxidation product of a developing agent, such as the groups capable of being released under an alkaline condition as described in Japanese Patent Publication Open to Public Inspection (hereinafter referred to as Japanese Patent O.P.I. Publication) No. 228444/1986, and the groups described in Japanese Patent O.P.I. Publication No. 133734/1981. Y is preferably a hydrogen atom.

Accordingly, the compound of the present invention represented by Formula I is represented preferably by the following Formula II:

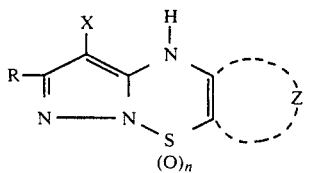

wherein R, X and Z represent the same as those defined for R, X and Z in Formula I.

The 5- to 7-membered heterocycle represented by Z may be either saturated or unsaturated, and the hetero atom contained therein is preferably a nitrogen, sulfur or oxygen atom. Accordingly, the compounds represented by Formula II is represented preferably by Formulas IIa through III.

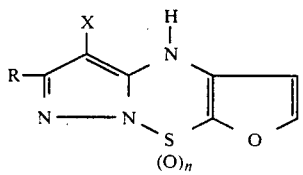
Formula IIa

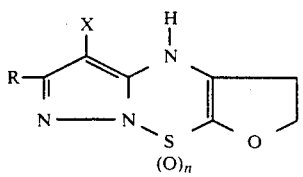
Formula IIb

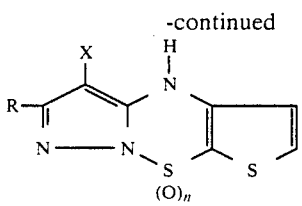
Formula IIc

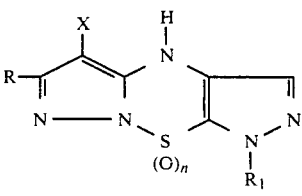
Formula IId

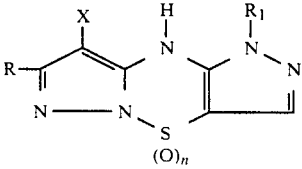
Formula IIe

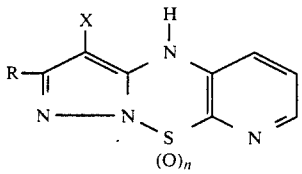
Formula IIf

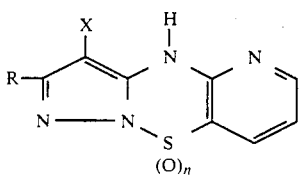
Formula IIg

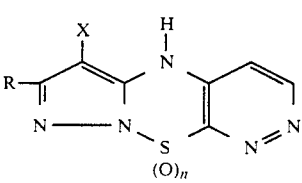
Formula IIh

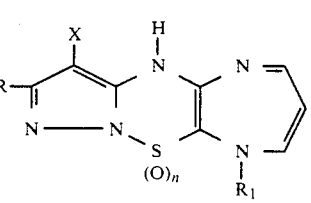
Formula IIi

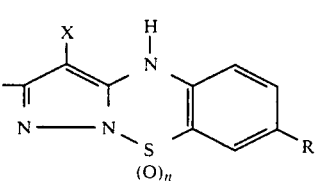
Formula IIj

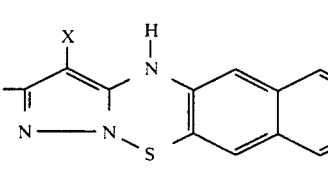
Formula IIk

-continued

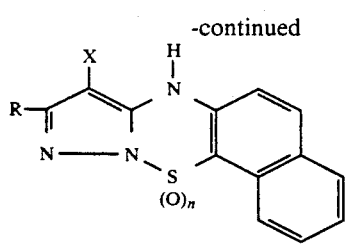

Formula III wherein R and X represent the same as those defined for R and X in Formula I; $R_1$ represents a substituent such as alkyl, aryl, alkenyl, cycloalkyl, sulfonyl, acyl, carbamoyl, sulfamoyl, alkoxycarbonyl and aryloxycarbonyl groups; and R" represents a hydrogen atom or a substituent.

The condensed ring in Formulas IIa through III may have a substituent.

The typical examples of the compounds of the present invention are hereunder illustrated.

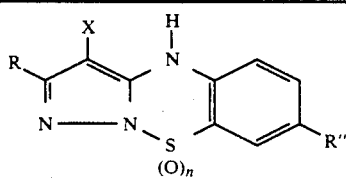

Formula IIj

| No. | R | R" | X | n |
|---|---|---|---|---|
| 1 | $CH_3-$ | H | H | 2 |
| 2 | $i\text{-}C_3H_7-$ | H | H | 2 |
| 3 | $t\text{-}C_4H_9-$ | H | Cl | 2 |
| 4 | phenyl- | H | H | 2 |
| 5 | $CH_3-$ | H | H | 2 |
| 6 | furyl- | H | H | 2 |
| 7 | $C_{14}H_{29}SO_2NH$-phenyl- | H | Cl | 2 |
| 8 | $CH_3-$ | $-NHSO_2C_{16}H_{33}$ | H | 2 |
| 9 | $CF_3-$ | $-NHCOCH(C_4H_9)O$-(2-$t\text{-}C_5H_{11}$-4-$C_5H_{11}(t)$-phenyl) | H | 2 |
| 10 | $C_8H_{17}\text{-}i$ | H | Cl | 2 |
| 11 | $C_{10}H_{21}O$-phenyl- | H | H | 2 |
| 12 | (3-$t\text{-}C_8H_{17}CONH$)phenyl- | H | H | 2 |
| 13 | (2-$NHCOCH_3$)phenyl- | $-NHCOCH_2CH_2CH_2SO_2C_{12}H_{25}$ | H | 2 |

-continued

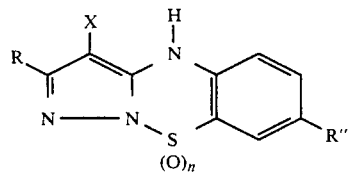
Formula IIj

| | R | X | R″ | n |
|---|---|---|---|---|
| 14 | CF$_3$— | —NHCOCH$_2$CH$_2$O—⟨Ar: 2-t-C$_5$H$_{11}$, 4-C$_5$H$_{11}$(t)⟩ | —SCH$_2$CH$_2$COOH | 2 |
| 15 | t-C$_4$H$_9$— | —NHCOCH(C$_4$H$_9$)O—⟨Ar: 2-t-C$_5$H$_{11}$, 4-C$_5$H$_{11}$(t)⟩ | H | 2 |
| 16 | i-C$_3$H$_7$— | —NHCOCH(C$_2$H$_5$)O—⟨Ar: 3-C$_{15}$H$_{31}$⟩ | —OCH$_2$CH$_2$OH | 2 |
| 17 | CH$_3$— | —NHCO(CH$_2$)$_8$CH=CH$_2$ | ⟨1-pyrazolyl⟩ | 2 |
| 18 | ⟨2-(NHSO$_2$N(CH$_3$)$_2$)phenyl⟩ | —NHCOC$_{10}$H$_{21}$ | —S—⟨Ar: 2-OC$_4$H$_9$, 4-C$_8$H$_{17}$(t)⟩ | 2 |
| 19 | CF$_3$— | —NHCOC$_{14}$H$_{29}$ | —O—⟨C$_6$H$_4$—COOH (4-)⟩ | 2 |
| 20 | ⟨3-C$_{10}$H$_{21}$O-phenyl⟩ | H | —SCH$_2$CH$_2$COOCH$_3$ | 2 |
| 21 | CH$_3$— | —NHCOC$_{10}$H$_{21}$ | Cl | 1 |
| 22 | ⟨phenyl⟩ | —NHCOCH(C$_2$H$_5$)O—⟨Ar: 2-C$_5$H$_{11}$(t), 4-C$_5$H$_{11}$(t)⟩ | H | 1 |
| 23 | CF$_3$— | —NHCOC$_{14}$H$_{29}$ | H | 1 |
| 24 | CF$_3$— | —NHCOCH(C$_4$H$_9$)O—⟨Ar: 2-C$_5$H$_{11}$(t), 4-C$_5$H$_{11}$(t)⟩ | Cl | 1 |

-continued
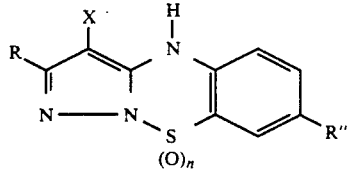
Formula IIj
| | R | (NHCO...) | R'' | n |
|---|---|---|---|---|
| 25 | (t)C$_4$H$_9$— | —NHCOC$_8$H$_{17}$(t) | H | 1 |
| 26 | CH$_3$— | —NHCOCH$_2$CH$_2$CH$_2$O—C$_6$H$_3$(C$_5$H$_{11}$(t))$_2$ | —OCH$_2$CH$_3$ | 1 |
| 27 | CH$_3$— | —NHCO(CH$_2$)$_8$CH═CH$_2$ | H | 1 |
| 28 | i-C$_3$H$_7$— | —NHCOC$_8$H$_{17}$(t) | Cl | 1 |
| 29 | i-C$_3$H$_7$— | —NHCOCH$_2$CH$_2$CH$_2$O—C$_6$H$_3$(C$_5$H$_{11}$(t))$_2$ | H | 1 |
| 30 | o-CH$_3$C$_6$H$_4$(NHCOC$_{14}$H$_{29}$) | H | —SCH$_2$CH$_2$OH | 1 |
31. 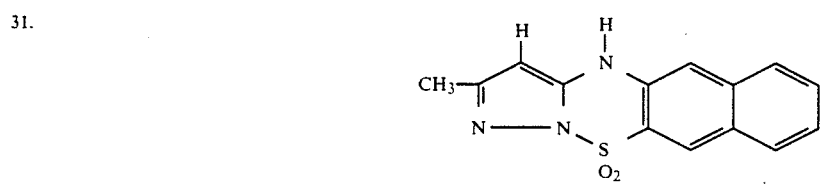
32. 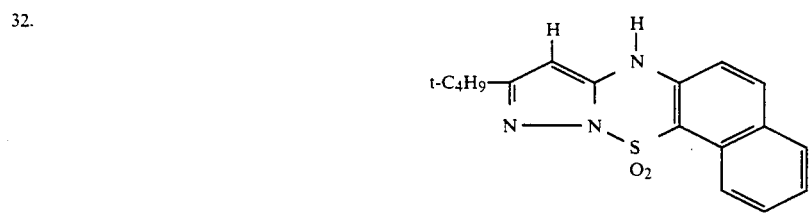
33. 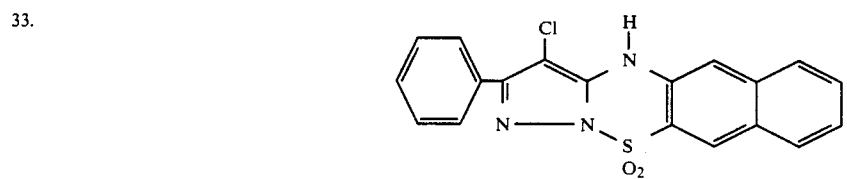
34. 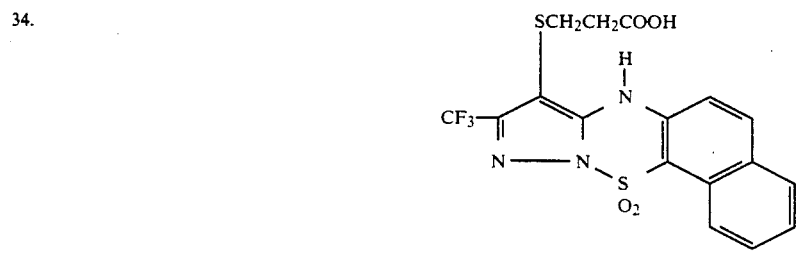

-continued
Formula IIj
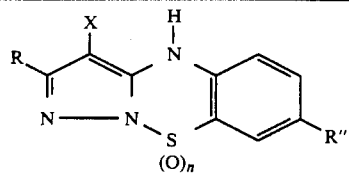
35. 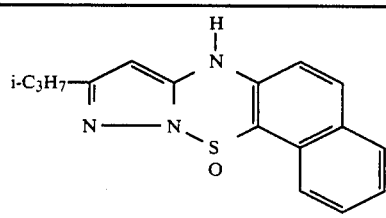
36. 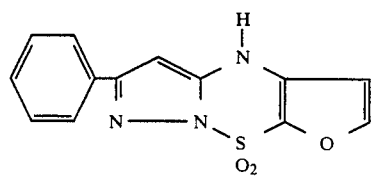
37. 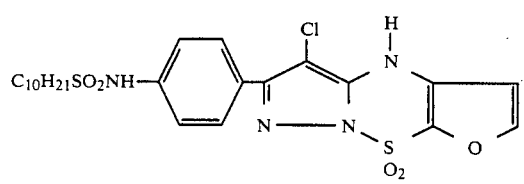
38. 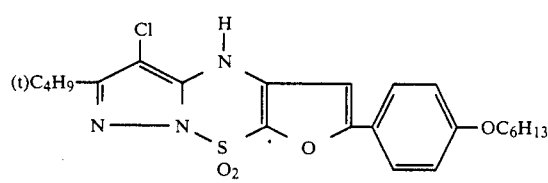
39. 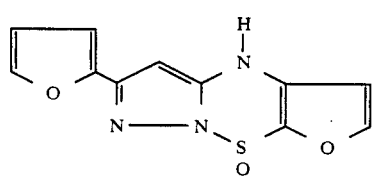
40. 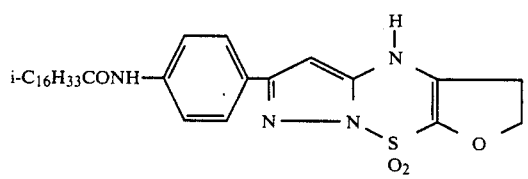
41. 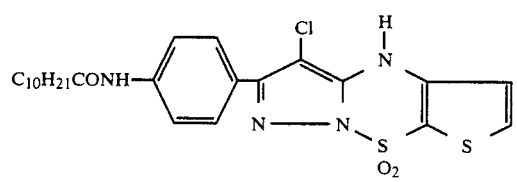
42. 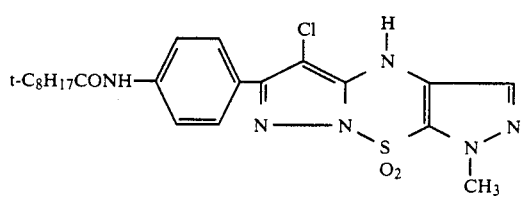

| | |
|---|---|
| 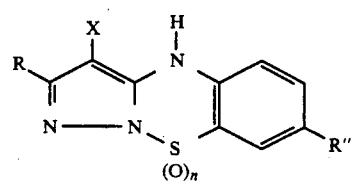 | Formula IIj |
43.
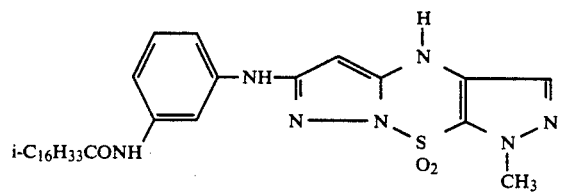
44.
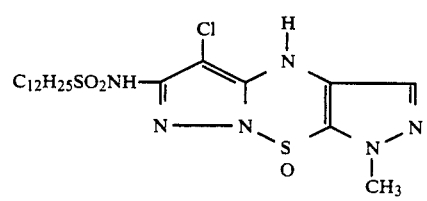
45.
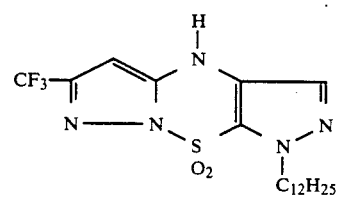
46.
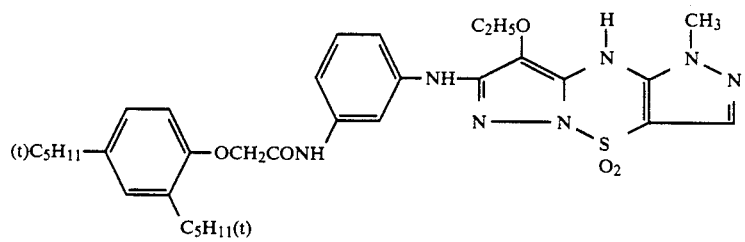
47.
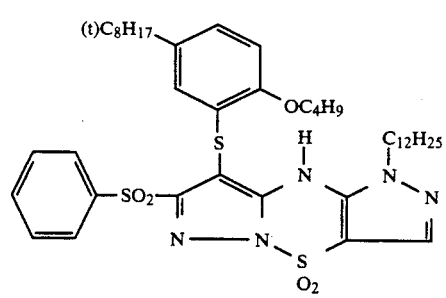
48.
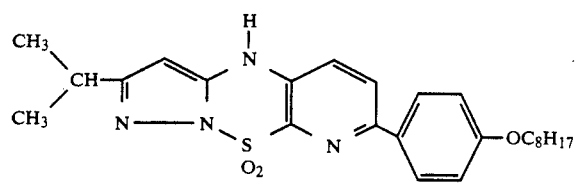

-continued
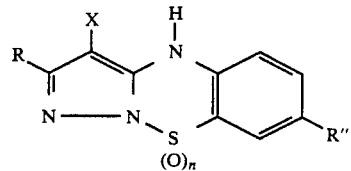
Formula IIj
49. 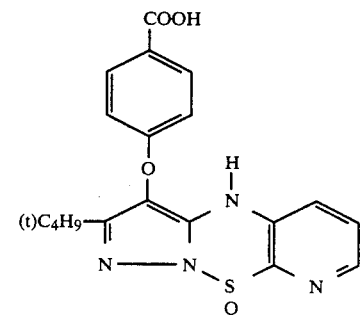
50. 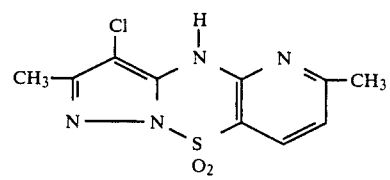
51. 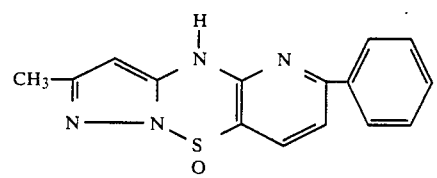
52. 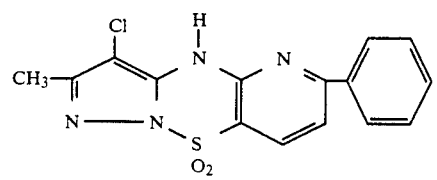
53. 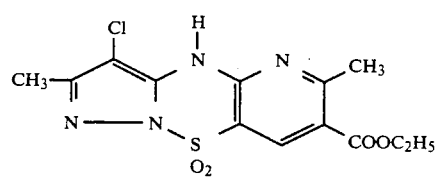
54. 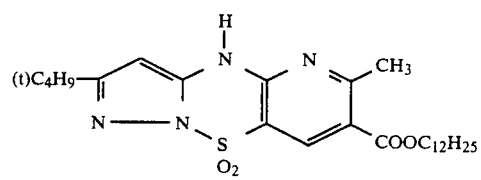
55. 

-continued
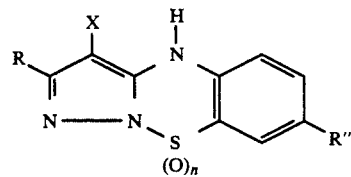
Formula IIj
56. 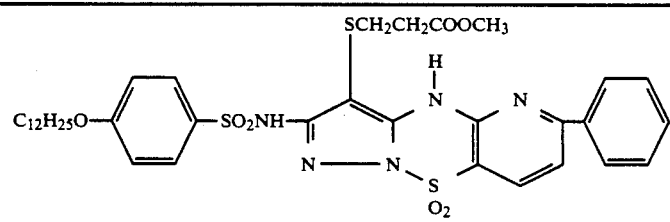
57. 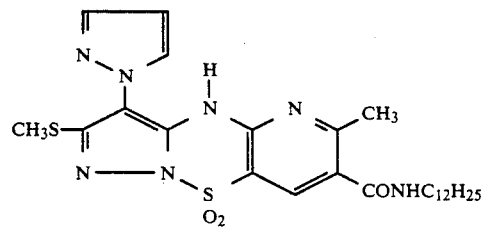
58. 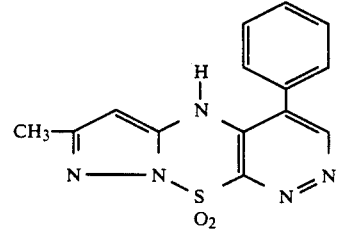
59. 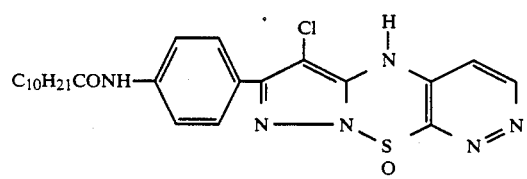
60. 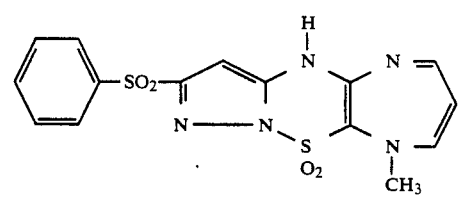
61. 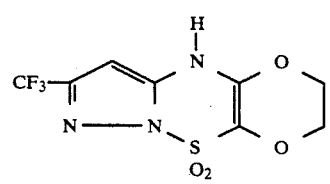
62. 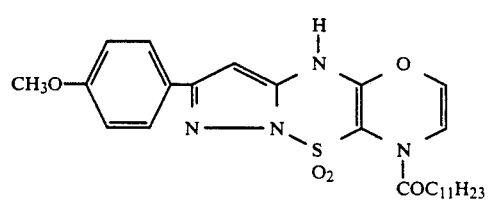

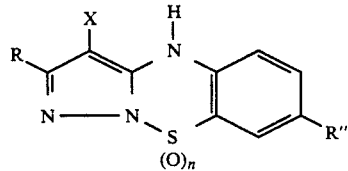

Formula IIj

63. 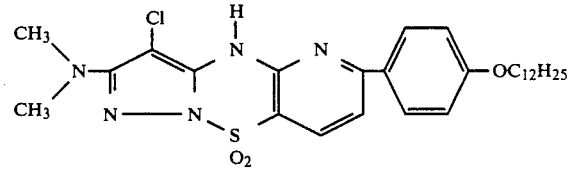

64. 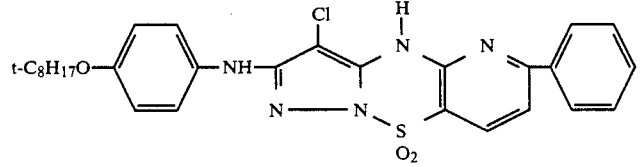

The foregoing couplers of the present invention can be synthesized according to the synthesis method described in Journal of Heterocyclic Chemistry, Vol. 13, p. 395 (1976).

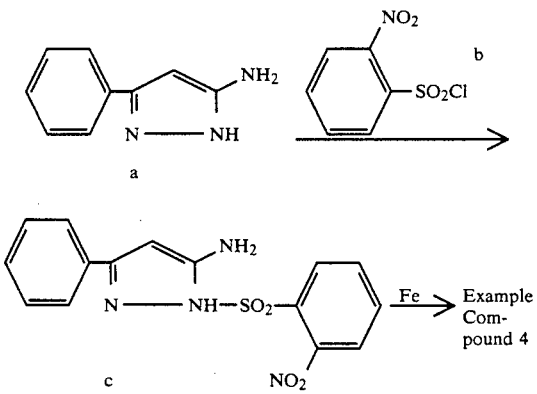

Synthesis of Intermediate c

To 1500 ml of chloroform were added 32 g of Compound a, 44 g of Compound b and 22 g of triethylamine, and then the mixture was heated for 3 hours under refluxing. Next, chloroform was removed by vacuum distillation. To the residue were added 50 ml of ethanol and 300 ml of water, and the resulting crystal was filtered. It was recrystallized from ethanol to obtain 48 g of Intermediate c, which was identified with $^1$HNMR, IR and mass spectrum.

Synthesis of Compound 4

Intermediate c 34 g was dissolved in 200 ml of acetic acid by heating at 70° C. under stirring, and then 15 g of iron powder was added little by little over a period of 1 hour, followed by stirring at 70° C. for 2 hours. The reaction mixture was filtered to remove the iron powder while heating. The filtrate was poured into 2000 ml of ice water. The precipitated crystals were filtered, and then recrystallized from ethanol to obtain 8 g of Compound 4, which was identified with $^1$HNMR, IR and mass spectrum.

The coupler of the invention is used usually in an amount of $1 \times 10^{-3}$ to 1 mol, preferably $1 \times 10^{-2}$ to $8 \times 10^{-1}$ mol of the silver halide.

The coupler of the invention can be used together with couplers of other types.

The methods and techniques that are employed for conventional dye-forming couplers can be applied also to the coupler of the present invention.

The coupler of the invention can be used as a color photographic image-forming element in any color developing process such as a coupler-in-developer process and a coupler-in-emulsion process. In the coupler-in-developer process, the coupler of the invention is added to a developer in the form of an alkaline aqueous solution or an organic solvent (e.g. ethanol) solution.

In the coupler-in-emulsion process, the coupler of the invention is incorporated into a light-sensitive material.

It is preferable to incorporate the coupler of the invention into a silver halide emulsion, then to apply this emulsion on a support to prepare a light-sensitive material. The coupler of the invention can be used for light-sensitive materials such as negative and positive color films and a color photographic paper.

The coupler of the invention may be applied either to monochrome or multicolor light-sensitive material. The coupler of the invention may be incorporated into any layer. Usually, it is incorporated into a green-sensitive silver halide emulsion layer and/or a red-sensitive silver halide emulsion layer. The multicolor light-sensitive material comprises the dye image-forming component layers sensitive to each spectral region of the three primary colors. Each component layer may be composed of a single emulsion layer or multiple emulsion layers sensitive to specific spectral regions. The component layers including the light-sensitive emulsion layers may be provided in various orders. The conventional multicolor light-sensitive material comprises a support and provided thereon a red-sensitive silver halide emulsion layer containing a cyan coupler, a green-sensitive silver halide emulsion layer containing a magenta coupler and a blue-sensitive silver halide emulsion layer containing a yellow coupler.

The light-sensitive material may have additional layers such as a filter layer, an intermediate layer, a protective layer and a subbing layer. The coupler of the invention may be incorporated into the emulsion according to a conventional method.

Silver halides used in the invention are silver chloride, silver chlorobromide and silver chloroiodobromide, and may be a mixture of silver chloride and silver bromide. Where a higher developing rate is particularly requested, it is preferable that chlorine is contained in silver halide. Particularly preferred are silver chloride, silver chlorobromide and silver chloroiodobromide each containing at least 1% of silver chloride.

The silver halide emulsion can be chemically and optically sensitized to a desirable wavelength region by a conventional method.

To prevent fogging and maintain stability of the photographic properties, an antifogging agent and a stabilizer may be added to the light-sensitive materials.

There may be added to the light-sensitive materials an antistain agent, a dye image stabilizer, a UV absorber, an antistatic agent, a matting agent and a surface active agent.

The light-sensitive material that contains the coupler of the invention are processed by a conventional method including developing, bleaching, fixing and washing to form an image.

EXAMPLES

The present invention is hereunder described in more details referring to the following examples.

EXAMPLE 1

On a paper support laminated with polyethylene on both sides were formed the following layers in order to prepare a red-sensitive color photographic material Sample 1. An amount of each compound is per $m^2$, unless otherwise specified (an amount of silver halide is a value converted to silver). First layer: a red-sensitive emulsion layer: containing 1.2 g of gelatin, 0.30 g of red-sensitive silver chlorobromide emulsion containing 96 mol% of silver chloride, and $9.1 \times 10^{-4}$ mol of a comparative cyan coupler A dissolved in 1.35 g of dioctyl phosphate; Second layer: a protective layer: containing 0.5 g of gelatin, to which there was added 2,4-dichloro-6-hydroxy-s-triazine sodium salt as hardener in an amount of 0.017 g per of gelatin.

Next, Sample Nos. 2 through 8 of the invention were prepared in the same manner as in Sample 1, except that comparison coupler A was replaced with the couplers of the same amount as that of comparison coupler a as shown in Table 1.

Sample Nos. 1 through 8 were exposed through an optical wedge according to a conventional method, and then subjected to development under the following conditions:

| Processing | | |
| --- | --- | --- |
| Color Developing | 38° C. | 3 min. 30 sec. |
| Bleach-fixing | 38° C. | 1 min. 30 sec. |
| Stabilizing or Washing | 25–30° C. | 3 min. |
| Drying | 75–80° C. | 2 min. |

The composition of each processing solution was as follows:

| Color Developer | |
| --- | --- |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-($\beta$-methanesulfonamideethyl)aniline sulfate | 5.5 g |
| Fluorescent whitening agent (4,4'-diaminostilbene disulfonate) | 1.0 g |
| Potassium hydroxide | 2.0 g |
| Water to | 1 l |
| pH was adjusted to 10.20. | |
| Bleach-fixer | |
| Ferric ammonia ethylenediamine tetraacetate dihydrate | 60 g |
| Ethylenediamine tetraacetic acid | 3 g |
| Ammonium thiosulfate (70% solution) | 100 ml |
| Ammonium sulfite (40% solution) | 27.5 ml |

After adjusting pH to 7.1 with potassium carbonate or glacial acetic acid, water was added to 1 liter.

| | |
| --- | --- |
| 5-chloro-2-methyl-4-isothiazoline-3-one | 1.0 g |
| Ethylene glycol | 10 g |
| Water to | 1 l |

The dye densities of Sample Nos. 1 through 8 were measured with the densitometer Model KD-7R made by Konica Corporation. Each sample was then aged at 60° C. and 80% relative humidity for 14 days to evaluate the heat and moisture resistance of the dye images.

Further, each sample was subjected to illumination for 10 days with a xenon fadeometer, and then the density thereof was measured once again to evaluate a light fastness.

The results are summarized in Table 1, wherein the heat and moisture resistance and the light fastness are expressed in percentages of the residual dye images to the initial density of 1.0 after the stability tests.

Comparative coupler A

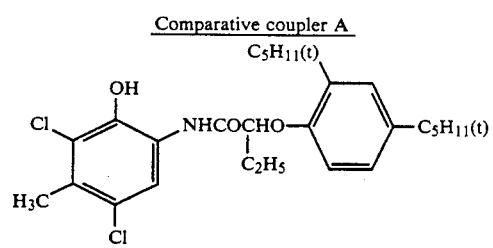

TABLE 1

| Sample No. | Coupler | Dye image residual rate (%) | |
| --- | --- | --- | --- |
| | | Heat and moisture resistance | Light fastness |
| 1 | Comparison A | 61 | 80 |
| 2 | Invention 7 | 87 | 84 |
| 3 | Invention 13 | 90 | 89 |
| 4 | Invention 14 | 90 | 85 |
| 5 | Invention 26 | 88 | 87 |
| 6 | Invention 37 | 85 | 83 |
| 7 | Invention 44 | 90 | 85 |
| 8 | Invention 61 | 86 | 86 |

As apparent from Table 1, the samples of the invention have the higher dye image residual rates and therefore, the more excellent resistances to heat, moisture and light than those of the comparative sample.

EXAMPLE 2

On a subbed triacetate film base were formed the following layers in order to prepare a red-sensitive color photographic material Sample 9. An amount of each compound is per m² (an amount of silver halide is a value converted to silver). First layer: a red-sensitive silver emulsion layer: containing 1.4 g of gelatin, 1.5 g of a red-sensitive silver iodobromide emulsion containing 4 mol% of silver iodide, and $8 \times 10^{-4}$ mol of comparative cyan coupler B dissolved in 1.1 g of tricresyl phosphate; Second layer: a protective layer: containing 1.5 g of gelatin, to which there was added sodium salt of 2,4-dichloro-6-hydroxy-s-triazine as a hardener in an amount of 0.017 g per g of gelatin.

Next, Sample Nos. 10 through 16 of the invention were prepared in the same manner as in Sample 9, except that comparison coupler B was replaced with the couplers of the same amount as that of comparison coupler B as shown in Table 2.

Each sample was exposed through an optical wedge in a conventional manner, and then developed according to the following color developing process:

Comparative coupler B

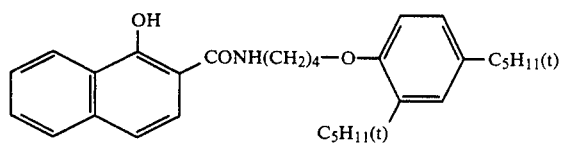

| Processing | | |
|---|---|---|
| Color developing | 38° C. | 3 min. 15 sec. |
| Bleaching | 38° C. | 6 min. 30 sec. |
| Washing | 38° C. | 3 min. 15 sec. |
| Fixing | 38° C. | 6 min. 30 sec. |
| Washing | 38° C. | 3 min. 15 sec. |
| Stabilizing | 38° C. | 1 min. 30 sec. |
| Drying | | |

The composition of each processing solution was as follows:

| Color Developer | |
|---|---|
| 4-amino-3-methyl-N-ethyl-N-(β-hydroxyethyl) aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Trisodium nitrilotriacetate monohydrate | 2.5 g |
| Potassium hydroxide | 1.0 g |

Water was added to 1 liter, and pH was adjusted to 10.6 with sodium hydroxide.

| Bleacher | |
|---|---|
| Ferric ammonium ethylenediamine tetraacetate | 100.0 g |
| Diammonium ethylenediamine tetraacetate | 10.0 g |
| Ammonium bromide | 150.0 g |
| Glacial acetic acid | 10.0 g |

Water was added to 1 liter, and pH was adjusted to 6.0 with aqueous ammonia.

| Fixer | |
|---|---|
| Ammonium thiosulfate | 175.0 g |
| Anhydrous sodium sulfite | 8.6 g |
| Sodium metasulfite | 2.3 g |

Water was added to 1 liter, and pH was adjusted to 6.0 with acetic acid.

| Stabilizer | |
|---|---|
| Formalin (37% aqueous solution) | 1.5 ml |
| Konidux made by Konica Corporation | 7.5 ml |
| Water to | 1 l |

The processed Sample Nos. 9 through 16 were treated in the same amount as in Example 1 to evaluate the resistances to heat, humidity and light.

The results are summarized in Table 2, wherein the heat and moisture resistance and the light fastness are expressed in percentages of the residual dye images to the initial density of 1.0 after the stability tests.

TABLE 2

| | | Dye image residual rate (%) | |
|---|---|---|---|
| Sample No. | Coupler | Heat and moisture resistance | Light fastness |
| 9 | Comparison B | 69 | 78 |
| 10 | Invention 4 | 91 | 79 |
| 11 | Invention 10 | 89 | 79 |
| 12 | Invention 15 | 88 | 81 |
| 13 | Invention 23 | 91 | 79 |
| 14 | Invention 32 | 85 | 78 |
| 15 | Invention 41 | 87 | 82 |
| 16 | Invention 49 | 90 | 77 |

It is apparent from Table 2 that the samples of the invention have the higher dye image residual rates and therefore, the more excellent resistances to heat, moisture and light than those of the comparative example.

EXAMPLE 3

On triacetyl cellulose film supports were formed the following layers in order to prepare a red-sensitive reversal color photographic materials Sample Nos. 17 through 22. First Layer: a red-sensitive emulsion layer: containing 1.4 g of gelatin, 0.5 g of a red-sensitive silver chlorobromide emulsion containing 96 mol% of silver chloride, and $9.1 \times 10^{-4}$ mol of the coupler dissolved in 1.5 g of dibutyl phthalate; Second layer: a protective layer: containing 0.5 g of gelatin, to which there was added sodium salt of 2,4-dichloro-6-hydroxy-s-triazine as a hardener in an amount of 0.017 g per g of gelatin.

Each sample was exposed through an optical wedge in a conventional manner, and then developed by the following processes:

| Reversal processing | | |
|---|---|---|
| First development | 6 min. | 38° C. |
| Washing | 2 min. | 38° C. |
| Reversal | 2 min. | 38° C. |
| Color development | 6 min. | 38° C. |
| Conditioning | 2 min. | 38° C. |
| Bleaching | 6 min. | 38° C. |
| Fixing | 4 min. | 38° C. |
| Washing | 4 min. | 38° C. |
| Stabilizing | 1 min. | 38° C. |
| Drying | | room temp. |

The composition of each processing solution was as follows:

| First developer | |
| --- | --- |
| Sodium tetrapolyphosphate | 2 g |
| Sodium sulfite | 20 g |
| Hydroquinone monosulfonate | 30 g |
| Sodium carbonate monohydrate | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide (0.1% solution) | 2 ml |
| Water to | 1000 ml |
| Reversal solution | |
| Hexasodium nitrilotrimethylenephosphonate | 3 g |
| Stannous chloride dihydrate | 1 g |
| p-Aminophenol | 0.1 g |
| Sodium hydroxide | 5 g |
| Glacial acetic acid | 15 ml |
| Water to | 1000 ml |
| Color developer | |
| Sodium tetrapolyphosphate | 2 g |
| Sodium sulfite | 7 g |
| Sodium tertiary phosphate dodecahydrate | 36 g |
| Potassium bromide | 1 g |
| Potassium iodide (0.1% solution) | 90 ml |
| Sodium hydroxide | 3 g |
| Citradinic acid | 1.5 g |
| N-ethyl-N-($\beta$-methanesulfonamideethyl)-3-methyl-4-aminoaniline sulfate | 11 g |
| Ethylenediamine | 3 g |
| Water to | 1000 ml |
| Conditioner | |
| Sodium sulfite | 12 g |
| Sodium ethylenediamine tetraacetate dihydrate | 8 g |
| Thioglycerine | 0.4 ml |
| Glacial acetic acid | 3 ml |
| Water to | 1000 ml |
| Bleacher | |
| Sodium ethylenediamine tetraacetate dihydrate | 2.0 g |
| Ferric ammonium ethylenediaminetetraacetate dihydrate | 120.0 g |
| Potassium bromide | 100.0 g |
| Water to | 1000 ml |
| Fixer | |
| Ammonium thiosulfate | 80.0 g |
| Sodium sulfite | 5.0 g |
| Sodium bisulfite | 5.0 g |
| Water to | 1000 ml |
| Stabilizer | |
| Formalin (37% aqueous solution) | 5.0 ml |
| Konidux made by Konica Corporation | 5.0 ml |
| Water to | 1000 ml |

The heat and moisture resistance and the light fastness of the resulting dye images of the processed samples were evaluated in the same manner as in Example 2. The results are summarized in Table 3.

TABLE 3

| Sample No. | Coupler | Dye image residual rate (%) | |
| --- | --- | --- | --- |
| | | Heat and moisture resistance | Light fastness |
| 17 | Comparison A | 59 | 81 |
| 18 | Invention 12 | 91 | 80 |
| 19 | Invention 20 | 88 | 81 |
| 20 | Invention 30 | 89 | 80 |
| 21 | Invention 35 | 87 | 83 |
| 22 | Invention 57 | 90 | 82 |

It can be seen from Table 3 that the samples of the invention have the higher dye image residual rates and therefore, the more excellent resistances to heat, moisture and light that the comparative sample.

What is claimed is:

1. A silver halide light-sensitive photographic material comprising a support and provided thereon photographic component layers including a silver halide light-sensitive emulsion layer containing a compound represented by the following Formula I:

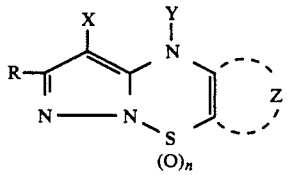

wherein R represents a hydrogen atom or a substituent; X and Y represent independently a hydrogen atom or a group capable of splitting off upon a reaction with an oxidation product of a developing agent; Z represents a nonmetallic group of atoms necessary to form a benzene ring, a naphthalene ring or a 5 to 7-membered heterocyclic ring; and n represents an integer of 1 or 2.

2. The photographic material of claim 1, wherein the substituent represented by R is an alkyl group, an aryl group, an anilino group, an acylamino group, a sulfonamide group, an alkylthio group, an arylthio group, an alkenyl group or a cycloalkyl group.

3. The photographic material of claim 1, wherein the group represented by X is a hydrogen atom, a halogen atom, an alkly group, an alkoxy group, an aryloxy group, a heterocyclicoxy group, an acyloxy group, a sulfonyloxy group, an alkoxycarbonyloxy group, an aryloxycarbonyl group, an alkyloxalyloxy group, an alkoxyoxalyloxy group, an alkythio group, an arylthio group, a heterocyclicthio group, an alkoxythiocarbonylthio group, an acylamino group, a sulfonamide group, a nitrogen-containing heterocyclic group having a bonding site on nitrogen, an alkoxycarbonylamino group, an aryloxycarbonylamino group, a carboxyl group, or a group represented by the following formula:

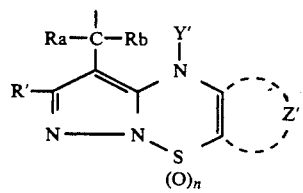

wherein R', Y' and Z' represent the same as those defined for R, Y and Z in Formula I, respectively; Ra and Rb represent independently a hydrogen atom, an alkyl group, an aryl group and a heterocyclic group; and n is 1 or 2.

4. The photographic material of claim 3, wherein X is a hydrogen atom or a halogen atom.

5. The photographic material of claim 1, wherein Y is a hydrogen atom.

6. The photographic material of claim 1 wherein the compound is represented by one of Formulas IIa to III:

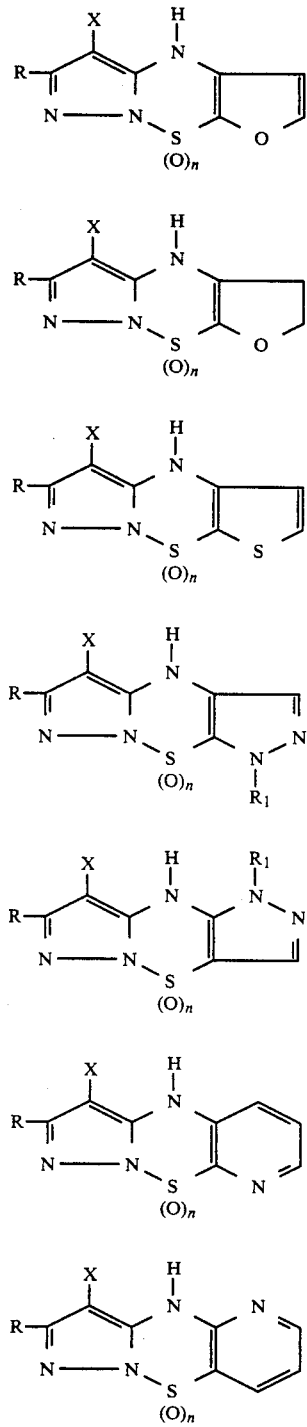

Formula IIa

Formula IIb

Formula IIc

Formula IId

Formula IIe

Formula IIf

Formula IIg

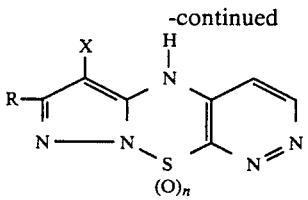

Formula IIh

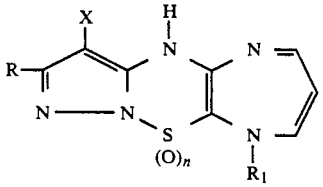

Formula IIi

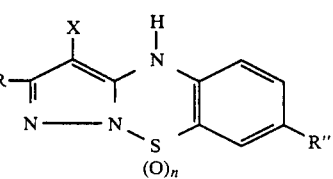

Formula IIj

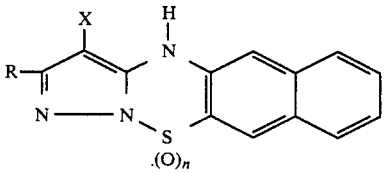

Formula IIk

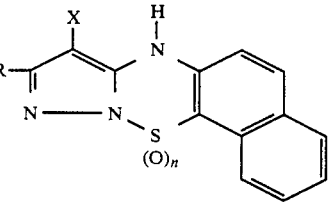

Formula II1 wherein R and X represent the same as those defined for R and X in Formula I, respectively; $R_1$ represents a substituent; and R" represents a hydrogen atom or a substituent.

7. The photographic material of claim 6, wherein the substituent represented by $R_1$ is an alkyl group, an aryl group, an alkenyl group, a cycloalkyl group, a sulfonyl group, an acyl group, a carbamoyl group, a sulfamoyl group, an alkoxycarbonyl group, or an aryloxycarbonyl group.

8. The photographic material of claim 1, wherein an addition amount of the compound is $1 \times 10^{-3}$ to 1 mole per mole of silver halide.

9. The photographic material of claim 8, wherein the addition amount is $1 \times 10^{-2}$ to $8 \times 10^{-1}$ mole per mole of silver halide.

* * * * *